United States Patent [19]

Uihlein

[11] 4,273,653
[45] Jun. 16, 1981

[54] MICROCHROMATOGRAPHIC SYSTEM FOR MEDICAMENT INTAKE CONTROL

[75] Inventor: Michael Uihlein, Kriftel, Fed. Rep. of Germany

[73] Assignee: Hoechst Aktiengesellschaft, Frankfurt am Main, Fed. Rep. of Germany

[21] Appl. No.: 122,732

[22] Filed: Feb. 19, 1980

[30] Foreign Application Priority Data

Feb. 20, 1979 [DE] Fed. Rep. of Germany ... 7904648[U]

[51] Int. Cl.$^3$ .......................................... B01H 15/08
[52] U.S. Cl. ................................ 210/198.3; 210/658; 422/58; 422/70
[58] Field of Search .......................... 422/58, 61, 70; 210/658, 198 C

[56] References Cited

U.S. PATENT DOCUMENTS

| | | | |
|---|---|---|---|
| 3,884,641 | 5/1975 | Kraffczyk et al. | 422/58 |
| 3,955,926 | 5/1976 | Fischer | 422/61 |
| 3,963,421 | 6/1976 | Jones | 210/658 |
| 4,159,193 | 6/1979 | Gauntley | 422/58 |
| 4,205,058 | 5/1980 | Wagner | 210/658 |

Primary Examiner—John Adee
Attorney, Agent, or Firm—Curtis, Morris & Safford

[57] ABSTRACT

Microchromatographic system which consists of a test tube serving as developing chamber (2) and being closed by a stopper (3), and a thin-layer plate or foil in the form of a strip (1) fitting into the test tube, said plate or foil being coated in its lower quarter with a layer for concentration and purification (a) which merges without interruption into a thin-layer chromatographic separating layer (b) covering the remainder of the strip.

3 Claims, 1 Drawing Figure

U.S. Patent
Jun. 16, 1981
4,273,653
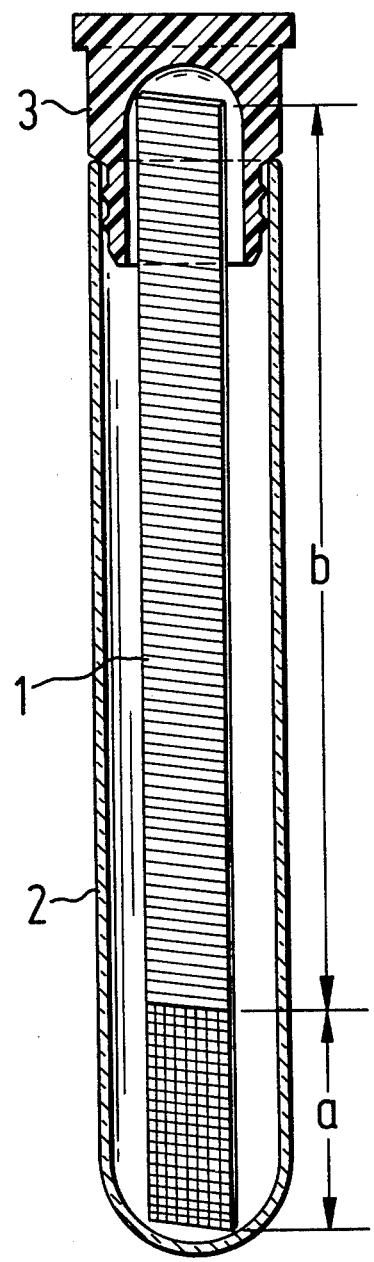

MICROCHROMATOGRAPHIC SYSTEM FOR MEDICAMENT INTAKE CONTROL

It is well-known that there are patients every once and again who will not, or not regularly, take a medicament which has been prescribed to them. As long as the situation is not known to the physician, he will attribute the therapy success naturally failing to appear to the inefficacy of the medicament. In future cases and for similar diseases, he will administer the allegedly ineffective medicament with discretion or possibly do without the same altogether. Moreover, the failure of his therapy will induce him to re-examine his actually correct diagnosis, which might result in a wrong judgment of the disease. Thus, it is very important for doctors to be able to find out whether the absence of the therapeutical success is to be attributed to the selection of an inappropriate medicament, or whether the alleged inefficacy may be explained merely by the fact that the patient himself caused the said failure by disregarding the intake prescription for the medicament.

Experience has shown that a control of this kind is certainly practicable if (a) the preparation is excreted for the most part renally in a homogeneous form (original substance or metabolite) and
(b) the renal excretion has been completed within 24 hours after the medicament intake.

This control should suitably be carried out by the detection of the original substance or the metabolite in the urine with the aid of thin-layer chromatography. Nevertheless, the thin-layer chromatographic control of medicament intake has not yet become a decisive factor in medical practice. The reason is to be seen in the fact that the methods of detection known so far require apparatuses which are too expensive and a chemical-analytical qualification of the personnel which as a rule may not be expected in medical practice.

Thus, the subject of the invention is the microchromatographic system which is shown diagrammatically by way of example in the accompanying drawing, which system consists of a test tube serving as developing chamber (2) and being closed by a stopper (3), and a thin-layer plate or foil in the form of a strip (1) fitting into the test tube, said plate or foil being coated in its lower quarter (a) with a layer for concentration and purification which merges without interruption into a thin-layer chromatographic separating layer (b) covering the remainder of the strip.

This thin-layer chromatographic system is designed in such a simple and suitable way that it is made possible therewith to detect the medicament or its metabolite in the urine in a reliable manner, without a chromatographic equipment and special reagents, while employing a solvent system (0.5 to 1 ml) which has been provided together with the device.

This microchromatographic system is determined for single usage.

The test strip is suitably a glass plate or foil whose dimensions are, for example, 100×8 mm. It is coated on one side like a thin-layer plate, i.e. in the lower quarter with diatomaceous earth or a silica gel having extremely wide pores and a specific surface of $\leq 1 m^2/g$ (concentration zone a), which merges without interruption into a separation zone (b) covering the remainder of the strip. Said separation zone consists of a silica gel having narrow pores and high specific surface, as it is typical of thin-layer chromatography.

The developing chamber consists preferably of a polypropylene test tube having an inner diameter of about 15 mm and a height of about 95 mm and a stopper. The dimensions have thus been designed in a way that only from 0.5 to 1 ml of solvent is required for the separation by way of thin-layer chromatography. Such a small amount of the solvent may be provided—in the composition best adapted for the respective purpose—in a fused ampule of amber glass or a glass vessel with a tear-off clip-on cap. A good reproducibility of the separation and thus of the medicament detection is achieved by the saturation of the vapor space with the solvent, as experience has shown. In the case of the microchromatographic system of the invention, this is possible in a particularly simple manner by shaking the solvent in the developing chamber prior to immersing the test strip.

The detection process is advantageously carried out in the following manner:

About 1 ml of urine is introduced into a test tube. By immersing the concentration zone for 10 to 30 seconds, the test strip is wetted with urine. The strip subsequently dried is placed into the developing chamber filled with the solvent, until the flow limit has almost reached the upper end of the test strip. Said test strip which has been dried once more is examined in the UV light for the presence of characteristic spots in the separating layer. The judgement may be facilitated by using a template.

The above-described microchromatographic system comprises all the advantages of a simple and reliable thin-layer chromatographic method. It meets a requirement long since present to provide a method which makes it possible to check whether a patient has actually taken the medicament prescribed.

The following Examples show the wide applicability of the process.

EXAMPLE 1

(a) 25 Milligrams, 50 mg, 100 mg and 150 mg of Nomifensine were administered as a single dose to four different patients at 17.00 hours. On the following morning the urine was collected, 1 ml each was filled into a sample glass, and the test strip was introduced with the concentration layer downwards. After 15 seconds each the test strip was removed, dried and put into another sample glass containing 1 ml of solvent consisting of 99.5% of tetrahydrofuran and 0.5% of aqueous ammonia. The sample glass was closed, and after 15 minutes the test strip was removed again. After drying, the strip was irradiated for 15 minutes with UV light (254 μm), whereupon a spot fluorescent in a white to light yellow shade was detected under the UV light at a distance of from 50 to 65 mm from the lower edge of the test strip. This spot is characteristic of Nomifensine. Fluorescent spots in the concentration layer and at the upper edge of the separating layer are always present and are insignificant.

(b) In a second test one patient each took Clomifensine (a mixture of Clobazam and Nomifensine in the ratio of 3:10), the first patient beeing administered 32.5 mg, the second 65 mg of the mixture, whereas the third patient was given a placebo. The urine was collected in the periods 0 to 2 hours, 2 to 4 hours, 4 to 6 hours and 6 to 8 hours after the administration. The following results were obtained:

| Dose | 0–2 h | 2–4 h | 4–6 h | 6–8 h |
|---|---|---|---|---|
| 32.5 mg | + | ++ | ++ | + |
| 65 mg | ++ | ++ | ++ | + |
| placebo | − | − | − | |

EXAMPLE 2

In a further test 150 mg of Carbocromen were administered to a patient. The urine was collected to 0 to 1 hour, 1 to 2 hours, 2 to 4 hours, 4 to 6 hours, 6 to 8 hours, 8 to 10 hours and 24 to 26 hours after the administration. The detection method was the same as has been described in Example 1, however, as solvent there was used the liquid separating from two parts by volume of chloroform, 3 parts by volume of isopropanol, one part by volume of glacial acetic acid and one part by volume of bidistilled water in a separating funnel as the lower phase. The test strip showed a white fluorescent spot in the range of from 38 to 42 mm from its lower edge, which spot is characteristic of the carboncromenic acid obtained from Carbocromen. The following result was obtained:

| Time | Result |
|---|---|
| 0 to 1 h | − |
| 1 to 2 h | + |
| 2 to 4 h | + |
| 4 to 6 h | + |
| 6 to 8 h | + |
| 8 to 10 h | (+) |
| 24 to 26 h | − |

What is claimed is:

1. Microchromatographic system, which consists of a test tube serving as developing chamber (2) and being closed by a stopper (3), and a thin-layer plate or foil in the form of a strip (1) fitting into the test tube, said plate or foil being coated in its lower quarter with a layer for concentration and purification (a) which merges without interruption into a thin-layer chromatographic separating layer (b) covering the remainder of the strip.

2. Thin-layer plate or foil in the form of a strip fitting into a test tube (1), which has been coated in its lower quarter with a layer for concentration and purification (a) which merges without interruption into a thin-layer chromatographic separating layer (b) covering the remainder of the strip.

3. Microchromatographic system as claimed in claim 1, wherein the test tube serving as developing chamber (2) consists of polypropylene.

* * * * *